US008603093B2

(12) United States Patent
Hakki

(10) Patent No.: US 8,603,093 B2
(45) Date of Patent: Dec. 10, 2013

(54) METHOD OF DETERMINING ACETABULAR CENTER AXIS

(76) Inventor: Sam Hakki, Bay Pines, FL (US)

( * ) Notice: Subject to any disclaimer, the term of this patent is extended or adjusted under 35 U.S.C. 154(b) by 1128 days.

(21) Appl. No.: 12/157,079

(22) Filed: Jun. 6, 2008

(65) Prior Publication Data

US 2008/0306558 A1 Dec. 11, 2008

Related U.S. Application Data

(60) Provisional application No. 60/933,710, filed on Jun. 7, 2007.

(51) Int. Cl.
*A61F 2/46* (2006.01)

(52) U.S. Cl.
USPC .......................................... 606/86 R; 606/91

(58) Field of Classification Search
USPC ........ 606/86 R, 91, 81, 87; 623/19.11–19.14, 623/22.11, 22.12, 22.15, 22.21–22.46
See application file for complete search history.

(56) References Cited

U.S. PATENT DOCUMENTS

| | | | | |
|---|---|---|---|---|
| 5,007,936 | A * | 4/1991 | Woolson | 128/898 |
| 6,395,005 | B1 * | 5/2002 | Lovell | 606/91 |
| 6,711,431 | B2 * | 3/2004 | Pratt et al. | 600/426 |
| 7,559,931 | B2 * | 7/2009 | Stone | 606/91 |
| 2002/0077540 | A1 | 6/2002 | Kienzle | |
| 2003/0153829 | A1 * | 8/2003 | Sarin et al. | 600/426 |
| 2004/0230199 | A1 * | 11/2004 | Jansen et al. | 606/91 |
| 2005/0065628 | A1 * | 3/2005 | Roose | 700/117 |
| 2005/0251026 | A1 * | 11/2005 | Stone | 600/424 |
| 2006/0094958 | A1 * | 5/2006 | Marquart et al. | 600/434 |
| 2008/0009952 | A1 * | 1/2008 | Hodge | 623/22.21 |

FOREIGN PATENT DOCUMENTS

| | | |
|---|---|---|
| DE | 103 11 454 A1 | 7/2004 |
| WO | WO 2004/030556 A2 | 4/2004 |
| WO | WO 2006/109022 A2 | 10/2006 |

OTHER PUBLICATIONS

Ehrig et al., A survey of formal methods for determining the centre of rotation of ball joints, Oct. 3, 2005, Journal of Biomechanics, vol. 39, Issue 15, pp. 2798-2809.*
Kang et al., Hip joint modeling for the control of the joint center and the range of motions, 2003.*
The Math Forum @ Drexel, http://mathforum.org/library/drmath/view/55109.html, 1999.*
Willis, Clarence Addison, Plane Geometry, 1999, pp. 119-121.*
Predicting Knee Replacement Damage in a simulator Machine.

* cited by examiner

*Primary Examiner* — Kevin T Truong
*Assistant Examiner* — Zade Coley
(74) *Attorney, Agent, or Firm* — Frijouf, Rust & Pyle P.A.

(57) ABSTRACT

An apparatus and method is disclosed for aligning the anteversion and the inclination of an acetabular prosthetic cup within an acetabulum of a patient. The apparatus and method comprises calculating the orientation of acetabulum center axis. The acetabular prosthetic cup is aligned relative to the calculated acetabulum center axis. The acetabulum center axis is calculated from selecting rim points located about the acetabulum of the patient.

4 Claims, 7 Drawing Sheets

METHOD OF DETERMINING ACETABULAR CENTER AXIS

CROSS-REFERENCE TO RELATED APPLICATIONS

This applications claims benefit of U.S. Patent Provisional application Ser. No. 60/933,710 filed 7 Jun. 2007. All subject matter set forth in provisional application Ser. No. 60/933,710 is hereby incorporated by reference into the present application as if fully set forth herein.

BACKGROUND OF THE INVENTION

1. Field of the Invention

This invention relates to surgery and more particularly to an apparatus and method for total hip arthroplasty in a patient.

2. Background of the Invention

A total hip arthroplasty in a patient involves the insertion of a prosthetic stem into femur of a patient. The prosthetic stem is connected to a hip ball head through a metallic neck. The hip ball head and the metallic neck of the arthroplasty replace the head and neck of the femur of a patient. An acetabular prosthetic cup is mounted within the acetabulum of a patient for receiving the hip ball for completing the total hip arthroplasty.

A critical stage in the total hip arthroplasty procedure is the orientation of the acetabular prosthetic cup within the acetabulum of the patient. Typically, the acetabular prosthetic cup is orientated with respect to the anterior pelvic plane (APP). Various computer aided navigation systems have been devised for assisting a surgeon in orientating an acetabular prosthetic cup within the acetabulum of the patient.

In many cases, the anterior pelvic plane (APP) does not provide an accurate orientation of an acetabular prosthetic cup within the acetabulum of the patient. A small error in correctly identifying the anterior pelvic plane (APP) results in significant errors in the placement of acetabular prosthetic cup. In some instances, the pelvic position introduces significant errors in the placement of acetabular prosthetic cup. In other instances, the anterior pelvic plane (APP) is not a specific indicator for the placement of the acetabular prosthetic cup in a specific patient. Some in the prior art recommended the use of ultrasound in identifying anterior pelvic plane (APP). The use of ultrasound was done with the patient in a supine position. Unfortunately, the accuracy was diminished when the patient was moved into the lateral decubitus position. Other in the prior art recommend acquiring the anterior pelvic plane (APP) in the supine position prior to turning the patient to the side, but this can be impractical and increases the operative time with possible compromise to sterility.

Therefore, it is an abject of this invention to provide an improved method of aligning an acetabular prosthetic cup within an acetabulum of a patient through the use of a calculated acetabulum center axis.

Another object of this invention is to provide an improved method of aligning an acetabular prosthetic cup within an acetabulum of a patient that provides more accurate results than orientation with respect to the anterior pelvic plane (APP).

Another object of this invention is to provide an improved method of aligning an acetabular prosthetic cup within an acetabulum of a patient that may be incorporated in a computer aided navigation system.

The foregoing has outlined some of the more pertinent objects of the present invention. These objects should be construed as being merely illustrative of some of the more prominent features and applications of the invention. Many other beneficial results can be obtained by modifying the invention with in the scope of the invention. Accordingly other objects in a full understanding of the invention may be had by referring to the summary of the invention and the detailed description describing the preferred embodiment of the invention.

SUMMARY OF THE INVENTION

The present invention is defined by the appended claims with specific embodiments being shown in the attached drawings. For the purpose of summarizing the invention, the invention relates to an improved method of aligning the anteversion and the inclination of an acetabular prosthetic cup within an acetabulum of a patient comprising determining the orientation of acetabulum center axis and aligning the acetabular prosthetic cup relative to the acetabulum center axis.

In a more specific embodiment of the invention, the step of determining the orientation of acetabulum center axis includes determining the orientation of acetabulum center axis through selected rim points about the rim of the acetabulum of the patient. The step of determining the orientation of acetabulum center axis includes computing the orientation of acetabulum center axis through a computer aided navigation system. The step of aligning the acetabular prosthetic cup relative to the acetabulum center axis includes aligning the acetabular prosthetic cup relative to an indicator generated by a computer aided navigation system.

In another embodiment of the invention, the invention is incorporated into a method of determining the acetabulum center axis of a patient comprising the steps of selecting three rim points (A, B, C) about the acetabulum of the patient. A first geometric point (D) is calculated to be substantially equidistant from the three rim points (A, B, C). A second geometric point (E) is calculated to be displaced outwardly from the first geometric point (D) and to be substantially equidistant from the three rim points (A, B, C). A line (D-E) intersecting the first geometric point (D) and the second geometric point (E) is created to provide a line indicative of the acetabulum center axis of a patient.

In a more specific embodiment of the invention, the step of selecting three rim points (A, B, C) about the acetabulum of the patient includes averaging at least three rim points to select each of the three rim points (A, B, C). The step of selecting the rim point (A) includes averaging at least three rim points adjacent to a ridge of the pelvic bone. The step of selecting the rim point (B) and the rim point (C) includes averaging at least three rim points on opposed sides of the acetabulum of the patent to produce the maximum separation between the rim point (B) and the rim point (C). The step of selecting the first geometric point (D) and the second geometric point (E) includes selecting the first geometric point (D) and the second geometric point (E) through a computer aided navigation system.

In another embodiment of the invention, the invention is incorporated into a method of determining the acetabulum center axis (D-E) of a patient comprising the steps of selecting three rim points (A, B, C) about the periphery of the acetabulum of the patient. A first geometric point (D) is calculated to be substantially equidistant from the three rim points (A, B, C). A second geometric point (E) is calculated to be displaced outwardly from the first geometric point (D) and to be substantially equidistant from the three rim points (A, B, C). A line (D-E) intersecting the first geometric point (D) and the second geometric point (E) is created to provide a line indicative of the acetabulum center axis of a patient.

In still another embodiment of the invention, the invention is incorporated into an apparatus for determining the acetabulum center axis of an acetabulum of a patient. The apparatus comprises a sensor for sensing selected points about the acetabulum of the patient. A calculator computes the acetabulum center axis of the patient. An indicator indicates the acetabulum center axis of a patient.

In still another embodiment of the invention, the invention is incorporated into an apparatus for determining an acetabulum center axis of an acetabulum of the patient: The apparatus comprises a sensor for sensing three rim points (A, B, C) about the acetabulum of the patient. A calculator calculates the spatial relationship of the three rim points for computing a first geometric point (D) substantially equidistant from the three rim points (A, B, C). The calculator computes a second geometric point (E) displaced outwardly from the first geometric point (D) substantially equidistant from the three rim points (A, B, C). An indicator indicates a line (D-E) intersecting the first geometric point (D) and the second geometric point (E) to provide a line indicative of the acetabulum center axis of a patient.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
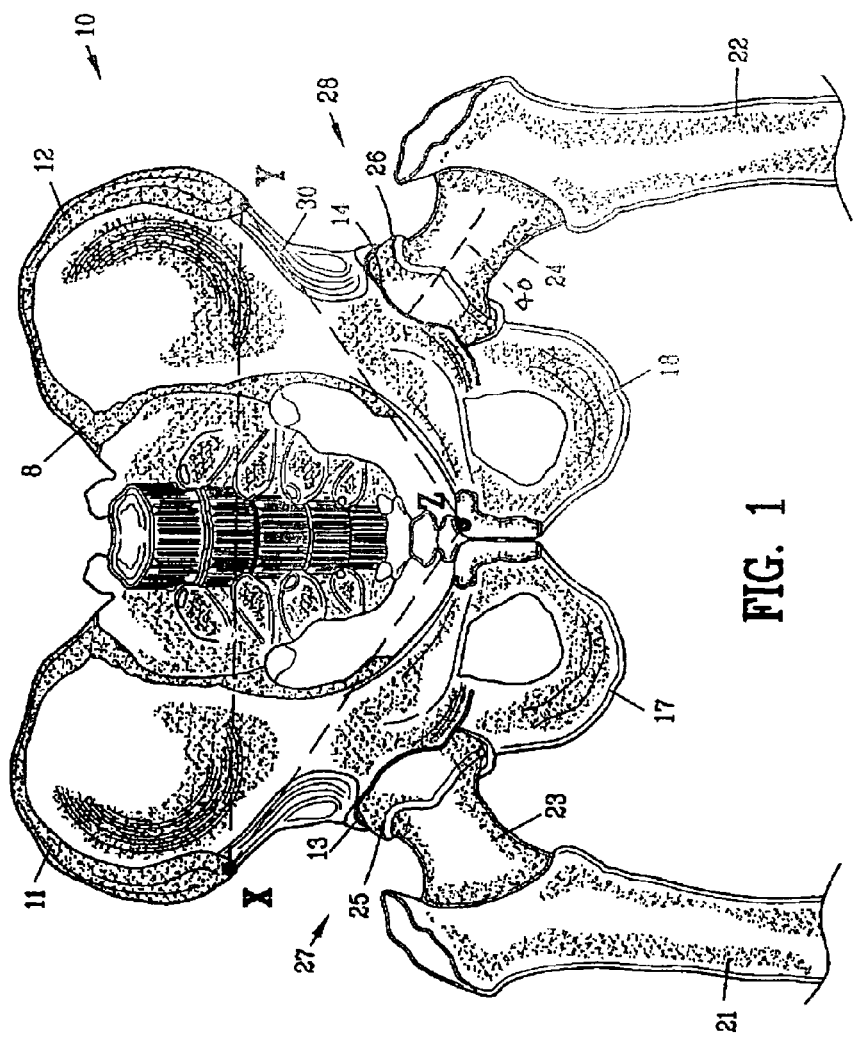
FIG. 1 is a front view of a pelvic bone with a right and left femur positioned within the right and left acetabulum.

FIG. 1 is a front view of a typical pelvic bone 8 of a patient 10. In this description, left and right refers to specific locations in the drawing and does not refer to the left and right as seen by the patient 10.

The pelvic bone 8 includes a left and a right illium 11 and 12, a left and a right acetabulum 13 and 14 and a left and a right pubis 17 and 18. A left and a right femur 21 and 22 includes a left and a right neck 23 and 24 for supporting a left and a right head 25 and 26. The left and right heads 25 and 26 engage with the left and right acetabulum 13 and 14 to form the left and right hip joints 27 and 28.

The pelvic bone 8 defines a left anterior superior illac spline (ASIS) shown as X. Similarly, the pelvic bone 8 defines a right anterior superior illac spline (ASIS) shown as Y. Furthermore, the pelvic bone 8 defines a pubic tubercle Z. The left and right anterior superior illac splines (ASIS) X and Y together with the pubic tubercle Z define an anterior pelvic plane (APP) 30. The anterior pelvic plane (APP) 30 is the classic reference for determining the version and inclination of an acetabular prosthetic cup within an acetabulum of a patient 10.

Figure 2:
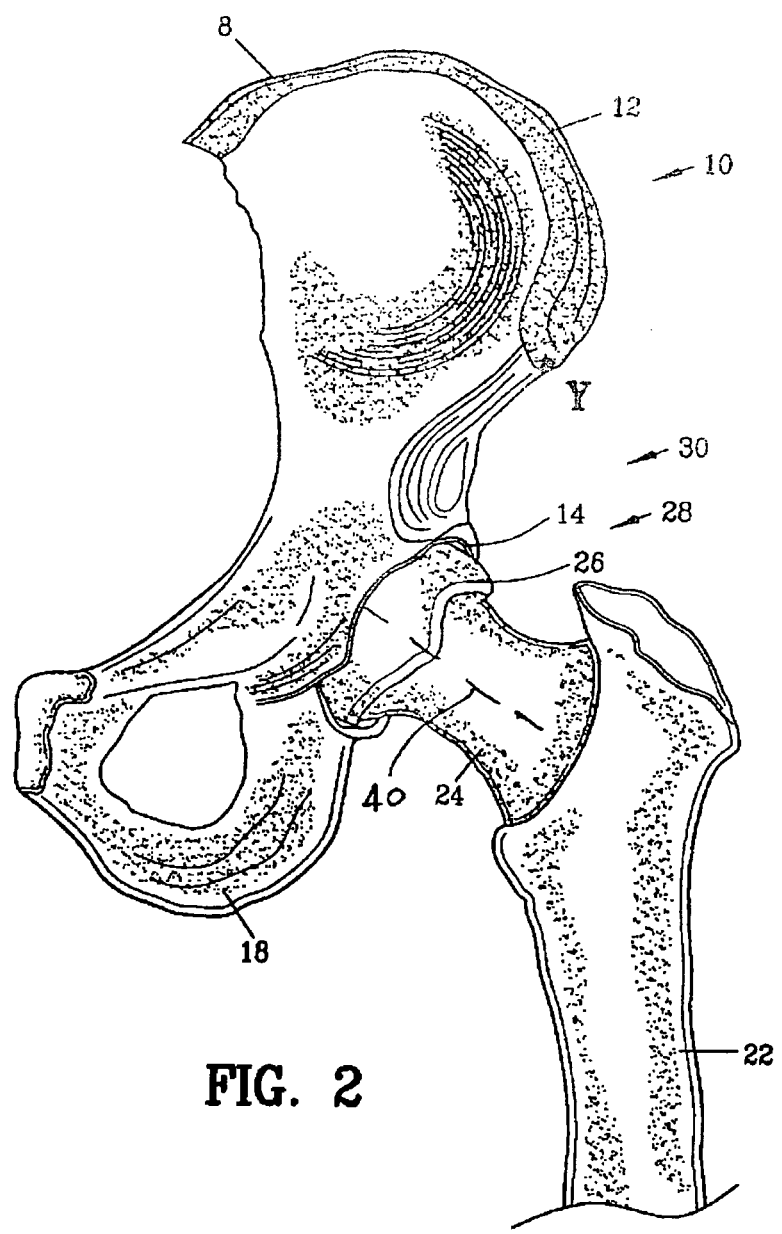
FIG. 2 is an enlarged view of a right portion of FIG. 1.

FIG. 2 is an enlarged view of a right portion of FIG. 1. In many cases, the anterior pelvic plane (APP) 30 does not provide an accurate orientation of the acetabular prosthetic cup within the acctabulum of the patient 10. An error in the orientation of the acetabular prosthetic cup within the acetabulum may be due to several factors. In many cases it is difficult to accurately determine the exact location of the left and right anterior superior iliac splines (ASIS) X and Y and the pubic tubercle Z due to the weight and or orientation of the patient 10. In other cases, the anterior pelvic plane (APP) is not indicative of tiac acetabulum center axis 40 of a patient 10 due to natural variations between patients and/or prior injuries to the pelvic bone 8.

Figure 3:
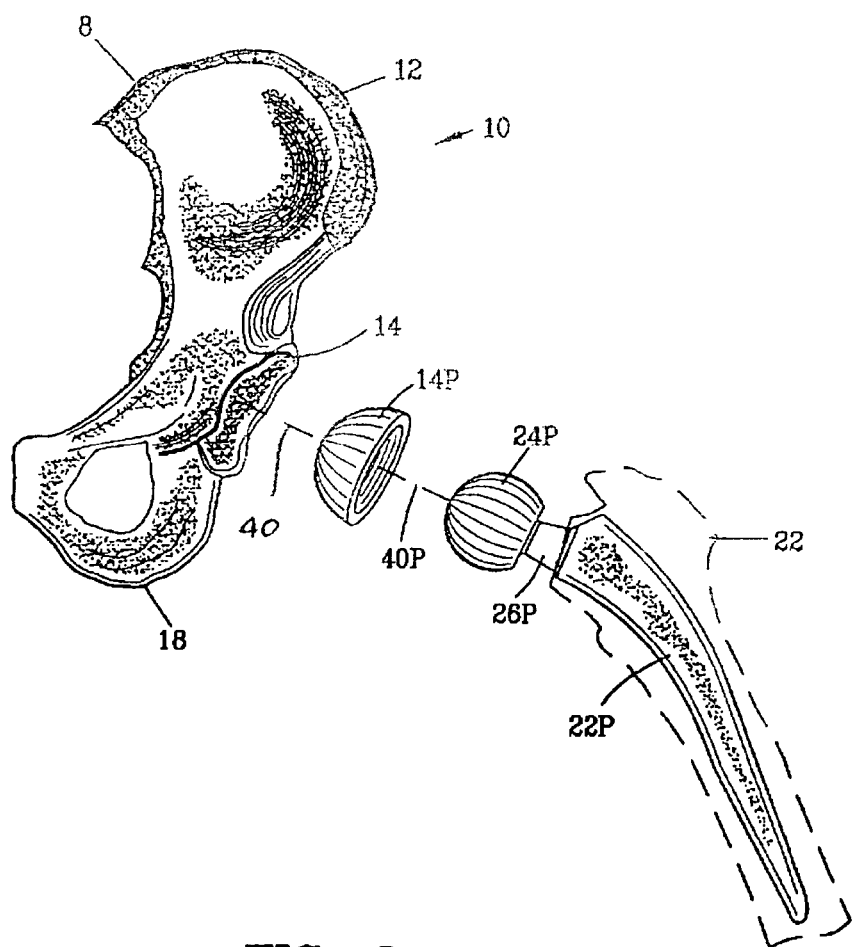
FIG. 3 is an exploded view illustrating a conventional hip prosthesis interposed between the pelvic bone and the left femur of FIG. 2.

FIG. 3 is an exploded view illustrating a conventional hip prosthesis interposed between the pelvic bone and the left femur of FIG. 2. The conventional hip prosthesis comprises an acetabular prosthetic cup 14P for insertion within the acetabulum of the patient 10. A prosthetic stem 22P is implanted into the femur 22 of the patient 10. The prosthetic stem 22P supports a prosthetic head 24P shown as a hip ball through a prosthetic neck 26P. The conventional hip prosthesis shown in FIG. 3 is by way of example and it shown be understood that the present invention may be used with virtually any type of hip prosthesis.

Referring back to FIG. 1, the left and right anterior superior illac splines (ASIS) X and Y together with the pubic tubercle Z define the anterior pelvic plane (APP) 30. Currently, the anterior pelvic plane (APP) 30 is used to identify the acetabular prosthetic cup 14P and acetabular orientation when navigating total hip arthroplasty (THA). The prior art has incorporated computer navigation for assisting in the placement of the acetabular prosthetic cup 14P in hip arthroplasty. Unfortunately, the reliability of using the anterior pelvic plane (APP) 30 as a reference system in a lateral decubitus position is jeopardized as the contra lateral ASIS is not readily accessible whether a pointer or the ultrasound methods are used. In addition, variation in thickness of subcutaneous tissue, the movement during the registration process and the anatomical variations of acetabular version among normal individuals resulted in major errors in the placement of the acetabular prosthetic cup 14P in hip arthroplasty.

The present invention provides an apparatus and a method of aligning the anteversion and the inclination of the acetabular prosthetic cup 14P within an acetabulum 14 of a patient 10 without the use of the anterior pelvic plane (APP) 30.

Figure 4:
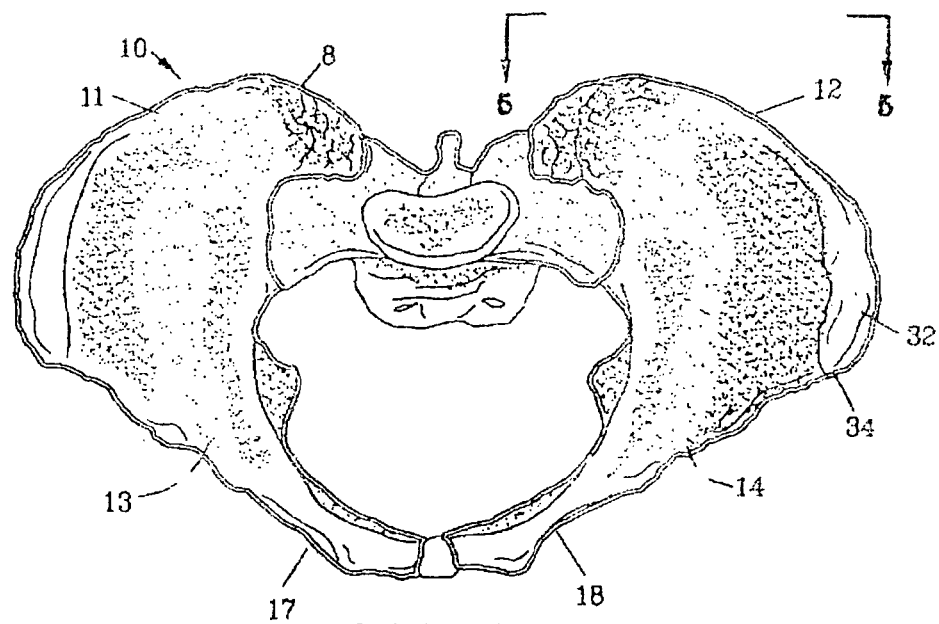
FIG. 4 is a top view of the pelvic bone of FIG. 1.
Figures 5, 6:
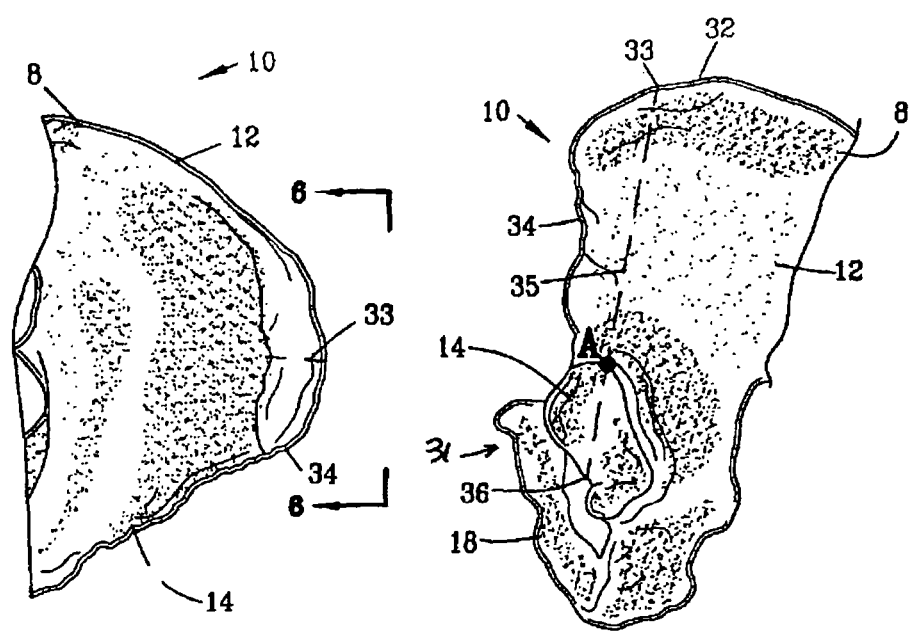
FIG. 5 is a view along line 5-5 in FIG. 4.
FIG. 6 is a view along line 6-6 in FIG. 5.

FIGS. 4-6 are various views of the pelvic bone shown in FIGS. 1-3. The orientation of the acetabular center plane (ACA) 31 and the corresponding acetabulum center axis 40 is determined through the selection of three rim points (A), (B) and (C) about the rim of the acetabulum 14 of the patient 10.

FIG. 5 is a magnified top view of the iliac tubercle 32. Preferably, a thickened region 33 of the tubercle 32 or center of iliac tubercle 32 is selected for the practice of the present invention. The thickened region 33 region is sometimes referred to as the peak or hump of the right illium 12 of the pelvic bone 8.

FIG. 6 illustrates a line 35 extending from the thick region 33 or center of iliac tubercle 32 to the center of the transverse ligament 36. The line 35 crosses the superior rim of the acetabulum 14 at a first or superior rim point (A) of registration. The first rim point (A) is located at the termination of a ridge 34 extending downwardly from a thickened region 33 of the tubercle 32 or center of iliac tubercle 32. The first rim point (A) is sometimes referred to as the dome of the acetabulum 14. The first rim point (A) is chosen so that the tilt of the pelvic bone 8 is kept constant.

Figure 7:
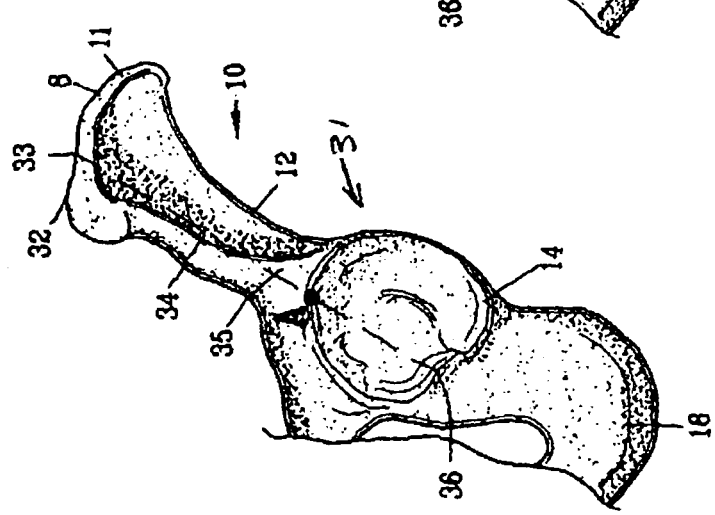
FIG. 7 is a magnified view of the pelvic bone and right acetabulum illustrating a first step of selecting a first rim point about the acetabulum of the patient.

FIG. 7 is a magnified view of the pelvic bone 8 and right acetabulum 14 illustrating a first step of selecting the first rim point (A) about the acetabulum 14 of the patient 10. The location of the first rim point (A) was previously described with reference to FIGS. 4-6. Preferably, the first rim point (A) is an average of at least three rim points adjacent to the line 35 extending from the thick region 33 or center of iliac tubercle 32 to the center of the transverse ligament 36.

Figure 8:
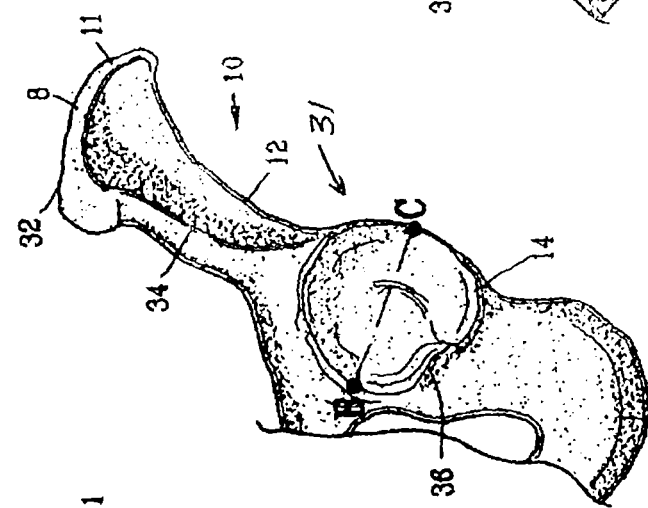
FIG. 8 is a view similar to FIG. 7 illustrating a second step of selecting a second and a third rim point about the acetabulum of the patient.

FIG. 8 is a view similar to FIG. 7 illustrating a second step of selecting a second or anterior rim point (B) and a third or posterior rim point (C) about the acetabulum 14 of the patient 10. The second rim point (B) and the third rim point (C) includes averaging at least three rim points on opposed sides of the acetabulum 14 to produce the maximum separation between the second rim point (B) and the third rim point (C). The distance between the second rim point (B) and the third rim point (C) represents the maximum diameter of the acetabulum 14 of the patient 10. An acetabular center plane (ACA) 31 extends through the first rim point (A), the second rim point (B) and the third rim point (C).

Figure 9:
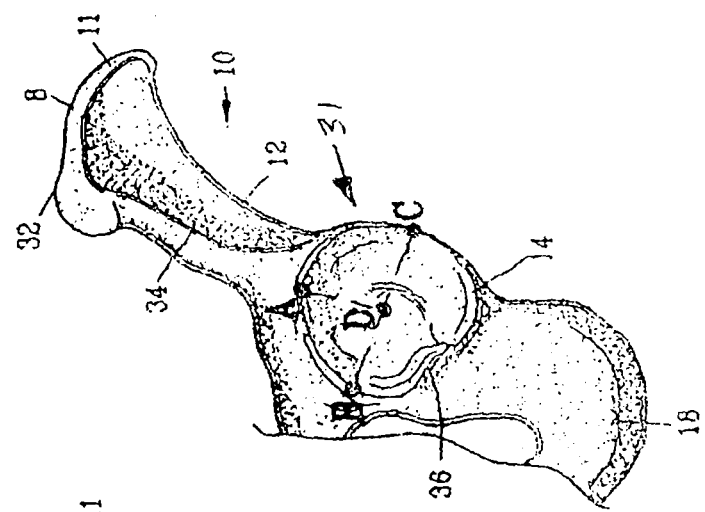
FIG. 9 is a view similar to FIG. 8 illustrating a third step of determining a first geometric point substantially equidistant from the first through third rim points.

FIG. 9 is a view similar to FIG. 8 illustrating a third step of determining a first geometric point (D) substantially equidistant from the first through third rim points (A, B, C). The distance AD is equal to the distance BD and is equal to the distance CD. Preferably, the third step of determining the first geometric point (D) is accomplished through a computer aided navigation system.

Figure 10:
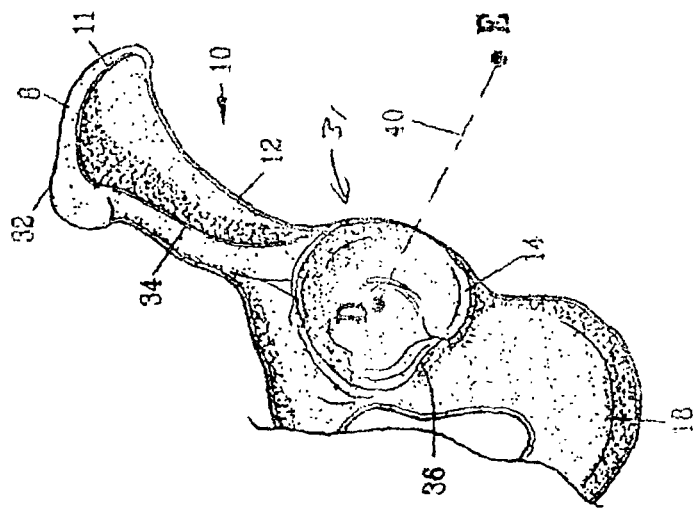
FIG. 10 is a view similar to FIG. 9 illustrating a fourth step of determining a second geometric point displaced outwardly from the first geometric point and substantially equidistant from the first through third rim points.

FIG. 10 is a view similar to FIG. 9 illustrating a fourth step of determining a second geometric point (E) displaced outwardly from the first geometric point (D) and substantially equidistant from the first through third rim points (A, B, C). The distance AE is equal to the distance BE and is equal to the distance CE. Preferably, the fourth step of determining the second geometric point (E) is accomplished through a computer aided navigation system.

Figure 11:
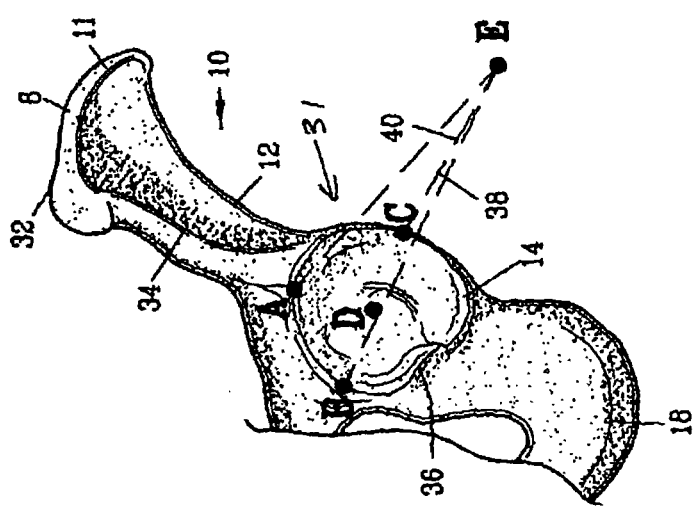
FIG. 11 is a view similar to FIG. 10 illustrating a fifth step of creating a line extending through the first and second geometric points to provide a line indicative of the acetabulum center axis of a patient.

FIG. 11 is a view similar to FIG. 10 illustrating a fifth step of creating a line 38 extending through the first geometric point (D) and the second geometric point (E). The line 38 extending through the first and second geometric points (D, E) provide a line indicative of the acetabulum center axis 40 of the acetabulum 14 of a patient 10. Preferably, the step of creating a line 38 extending through the first and second geometric points (D, E) is computed through a computer aided navigation system. A trial cup or trial reamer arm (not shown) having a passive sensor or an active sensor may be used to determine the second geometric point (E).

Figure 12:
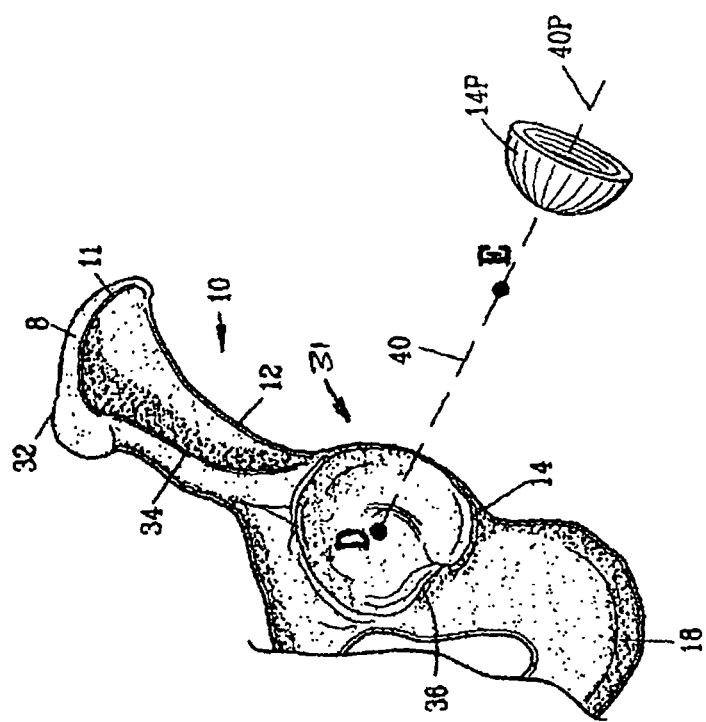
FIG. 12 is a view similar to FIG. 10 illustrating the alignment of an acetabular prosthesis cup with the center axis of the acetabulum of the patient.

FIG. 12 is a view similar to FIG. 10 illustrating the alignment of the axis 40P of the acetabular prosthetic cup 14P with the acetabulum center axis 40 of the acetabulum of the patient 10. The acetabulum center axis 40 indicates the center of that acetabulum 14 which will be the references for anteversion and inclanation angle estimation or guidline for the implantation of the acetabular prosthetic cup 14P. Under normal condition, the axis 40P of the acetabular prosthetic cup 14P is aligned with the acetabulum center axis 40 of the acetabulum 14 of the patient 10. Preferably, the step of aligning the axis 40P of the acetabular prosthetic cup 14P to the acetabulum center axis 40 of the acetabulum of the patient 10 is generated by a computer aided navigation system.

Figure 13:
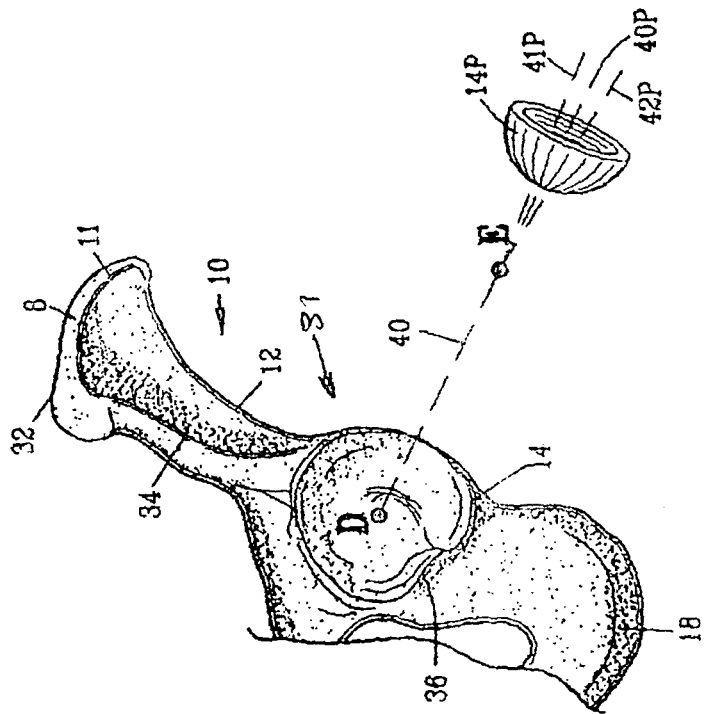
FIG. 13 is a view similar to FIG. 12 illustrating a variation in the alignment of the acetabular prosthesis cup with the center axis of the acetabulum of the patient.

FIG. 13 is a view similar to FIG. 12 illustrating a variation in the alignment of the acetabular prosthetic cup with the acetabulum center axis 40 of the acetabulum of the patient 10. FIG. 13 illustrates the present invention enables a surgeon to choose the desired version or inclination angle to suite the peculiar anatomy of each patient.

If the acetabulum 14 of a patient is protrusion, an angular correction from the acetabulum center axis 40 should be in the positive range as shown by the axis 41P of the acetabular prosthetic cup 14P. That means the acetabular prosthetic cup 14P will be smaller than the acetabulum 14. If the acetabulum of a patient is dysplastic, an angular correction from the acetabulum center axis 40 should be in the negative range as shown by the axis 42P of the acetabular prosthetic cup 14P. That means the acetabular prosthetic cup 14P is larger than the acetabulum 14 and some of the rim of the acetabular prosthetic cup is outside the acetabulum 14. This will enable the surgeon to make the proper adjustment in grossly abnormal acetabulum to achieve the ideal acetabular prosthetic cup position that is specific to each patient. However, no such adjustments are needed for determining the acetabular prosthetic cup version.

Results

The study compares through post-operative pelvis CT Scan, the ACA registration with that of APP using anterolateral inter-muscular mini invasive computerized THA. Of the 36 prospective patients enrolled, 2 were excluded with lack of full data. Age group ranged from 34 to 83 years with a mean of 63 years. 26 had primary osteoarthritis and 8 had avascular necrosis. Male:female=32/2. Mean body mass index=29.2. 11% had dysplastic acetabulum while 6% were protrusio.

34 out of the 36 consecutive patients were eligible for analysis of their hip data. Mean anatomic (CT-scan) Acetabular Version (ie Control) was 18.2(S.D. ±15.8), 23.0(S.D.±8.4) in ACA software , and 12.7(S.D.±12.1) in APP software. This reflects reliability of ACA software in identifying the version of the acetabulum.

Cup implant Version (CT-scan) was 22.97°(SD.±9.4), 23.0°(S.D.±8.4) in the ACA software and 12.7° (SD ±12.1) in the APP software. This reflects reliability and statistical superiority of ACA software in identifying the version of the cup implant (P=0.98), while the P value for the APP was significantly inferior to CT scan (P=0.0002).

The patients were divided into three groups according to anatomical variations of the acetabulum: (normal, protrusio and dysplastic).

In the first group, the size of the cup closely matched the size of the acetabulum (normal acetabulum), the anatomical (CT scan) Cup Version was 21.70(SD±21.70 (SD±8.8) in ACA software and 11.370(SD±10.5) in APP software. ACA was identical to CT scan (P=1.0) however, the APP was significantly inferior to CT scan. P=0.003.

In the second group, the size of the cup implant was smaller than the acetabulum (as in protrusio hips or in acetabulum with large osteophytes), the anatomical (CT scan) Version was 22.0° (SD±9.9), in ACA=22.8° (SD+9.5); and 14.3° (SD±15.1) in APP software. Interestingly, both ACA (P=0.89, and APP (P=0.38) were accurate. Still, ACA was more accurate but not to a statistical significance.

In the third group, the size of cup was larger than the acetabulum (as in dysplastic hips or the cup implant was larger by choice), the Version was 26.30 (SD=±7.1)in anatomic CT scan, 26.50 (SD±6.4) in ACA and 14.9 (SD±14.3) in APP software. Again, ACA was as accurate as CT-scan (P=0.96), while APP was less accurate (P=0.04). Finally, when we compared the accuracy of detecting the version of the cup implant between ACA and APP, there was a statistical difference between the two. (P=0.0001).

As for the inclination angle of the cup implant, mean anatomic (CT-scan) Cup Inclination Angle was 43.5° (S.D.±4.2), 43.5°(S.D.±7.5) in ACA software, and 41.1° (SD=±4.7). Both APP(P=0.44) and ACA (P=1.0) were accurate in detecting the inclination angle of the cup.

Similarly, we divided them in three groups; in the first group, the cup matched the acetabulum, the anatomic cup inclination angle was 42.7°(S.D.±3.6), ACA inclination of 43.10(SD±4.7) (p=0.73) and 40.4°(SD±4.7) for APP(P=0.097). Again, both software were accurate. In the second group, the cup size was smaller than the acetabulum the CT-scan inclination angle was 42.6 0(SD±4.0); 46.80(SD±6.6)in ACA and 42.60 (SD±4.0) in APP. Both were accurate.(P=0.92).

In the third group, the cup size was larger than the acetabulum, the anatomic cup inclination angle was 46.00 (SD=±4.8); 42.70 (SD±12.2) (P=0.45) for ACA and 42.00 (SD±5.5) for APP software. (P=0.12). This showed no statistical difference in both ACA and APP in detecting inclination angle in all types of acetabulae (normal, protrusio or dysplastic).(P=0.11).

Although ACA was statistically superior to APP in detection the version of the cup, both methods were within safety zone of Lewinnek with no complications related to implant or software use.

The present invention determines the orientation of an acetabular center plane (ACA) 31 and a corresponding acetabulum center axis 40 for aligning the acetabular prosthetic cup 14P relative to the acetabulum center axis 40. The acetabular center plane (ACA) 31 and the corresponding acetabulum center axis 40 is patient specific and independent of variations in the anatomy or the pelvic position. Furthermore, the acetabular center plane (ACA) 31 and the corresponding acetabulum center axis 40 relies on readily accessible anatomical landmarks of the acetabulum rather than the pelvic plane points.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A method of aligning an axis of an acetabular prosthetic cup with the acetabulum center axis of a patient, comprising the steps of:

selecting a rim point (A) on the acetabulum crossing a line extending between the center of iliac tubercle and the transverse acetabulum ligament;

selecting a second and a third rim point (B,C) on opposite sides of the acetabulum corresponding to the maximum diameter of the acetabulum;

determining a first geometric point (D) substantially equidistant: from the three rim points (A, B, C);

determining a second geometric point (E) displaced outwardly from the first geometric point (D) substantially equidistant from the three rim points (A, B, C);

creating a line (D-E) intersecting the first geometric point (D) and the second geometric point (E) to provide a line indicative of the acetabulum center axis of a patient; and implanting the prosthetic cup by aligning the axis of the acetabular prosthetic cup with the line indicative of the acetabulum center axis of the patient.

2. A method of aligning an axis of an acetabular prosthetic cup with the acetabulum center axis of a patient, comprising the steps of:

selecting a rim point (A) on the acetabulum crossing a line extending between the center of iliac tubercle and the transverse acetabulum ligament by averaging at least three rim points adjacent to the rim point (A);

selecting a second and a third rim point (B,C) on opposite sides of the acetabulum corresponding to the maximum diameter of the acetabulum by averaging at least three rim points adjacent to the rim points (B,C) respectively;

determining a first geometric point (D) substantially equidistant from the three rim points (A, B, C);

determining a second geometric point (E) displaced outwardly from the first geometric point (D) substantially equidistant from the three rim points (A, B, C);

creating a line (D-E) intersecting the first geometric point (D) and the second geometric point (E) to provide a line indicative of the acetabulum center axis of a patient; and implanting the prosthetic cup by aligning the axis of the acetabular prosthetic cup with the line indicative of the acetabulum center axis of the patient.

3. A method of determining the acetabulum center axis of a patient, comprising the steps of:

selecting a rim point (A) on the acetabulum crossing a line extending between the center of iliac tubercle and the transverse acetabulum ligament;

selecting a second and a third rim point (B,C) on opposite sides of the acetabulum corresponding to the maximum diameter of the acetabulum;

determining a first geometric point (D) substantially equidistant from the three rim points (A, B, C) through a computer aided navigation system;

determining a second geometric point (E) displaced outwardly from the first geometric point (D) substantially equidistant from the three rim points (A, B, C) through the computer aided navigation system; and creating a line (D-E) intersecting the first geometric point (D) and the second geometric point (E) to provide a line indicative of the acetabulum center axis of a patient.

4. A method of aligning an axis of an acetabular prosthetic cup with the acetabulum center axis of a patient, comprising the steps of:

selecting a rim point (A) located on the peripheral rim of the acetabulum of the patient in proximity to the dome of the acetabulum;

selecting a second and a third rim point (B,C) on opposite sides of the acetabulum corresponding to the maximum diameter of the acetabulum;

determining a first geometric point (D) substantially equidistant from the three rim points (A, B, C) through a computer aided navigation system;

determining, a second geometric point (E) displaced outwardly from the first geometric point (D) substantially equidistant from the three rim points (A, B, C) through the computer aided navigation system;

creating a line (D-E) intersecting the first geometric point (D) and the second geometric point (E) to provide a line indicative of the acetabulum center axis of a patient; and implanting the prosthetic cup by aligning the axis of the acetabular prosthetic cup with the line indicative of the acetabulum center axis of the patient.

\* \* \* \* \*